(12) United States Patent
Kertser

(10) Patent No.: US 11,524,130 B2
(45) Date of Patent: Dec. 13, 2022

(54) DEVICE, SYSTEM AND METHOD FOR THERMAL CAPNOGRAPHY

(71) Applicant: ORIDION MEDICAL 1987 LTD., Jerusalem (IL)

(72) Inventor: Michael Kertser, Bney Aish (IL)

(73) Assignee: ORIDION MEDICAL 1987 LTD., Jerusalem (IL)

( * ) Notice: Subject to any disclaimer, the term of this patent is extended or adjusted under 35 U.S.C. 154(b) by 1149 days.

(21) Appl. No.: 16/108,190

(22) Filed: Aug. 22, 2018

(65) Prior Publication Data

US 2019/0060591 A1 Feb. 28, 2019

Related U.S. Application Data

(60) Provisional application No. 62/551,302, filed on Aug. 29, 2017.

(51) Int. Cl.
*A61M 16/00* (2006.01)
*A61B 5/083* (2006.01)
(Continued)

(52) U.S. Cl.
CPC ....... *A61M 16/0057* (2013.01); *A61B 5/0836* (2013.01); *A61M 16/0841* (2014.02); *B81B 7/02* (2013.01); *G01N 25/18* (2013.01); *G01N 33/004* (2013.01); *G01N 33/497* (2013.01); *H01L 41/08* (2013.01); *A61B 5/0002* (2013.01); *A61B 5/082* (2013.01); *A61B 5/087* (2013.01); *A61B 2562/028* (2013.01); *A61M 16/006* (2014.02); *A61M 2016/0413* (2013.01); *A61M 2205/3334* (2013.01); *A61M 2205/3368* (2013.01); *A61M 2205/3375* (2013.01); *A61M 2230/432* (2013.01); *A61M 2230/50* (2013.01); *A61M 2230/65* (2013.01); *B81B 2201/031* (2013.01)

(58) Field of Classification Search
None
See application file for complete search history.

(56) References Cited

U.S. PATENT DOCUMENTS 3,698,384 A 10/1972 Jones
2008/0041172 A1 2/2008 Jaffe et al.
(Continued)

FOREIGN PATENT DOCUMENTS

DE 102010047159 A1 4/2012
EP 1391703 A1 2/2004
(Continued)

OTHER PUBLICATIONS

International Search Report and Written Opinion for PCT Application No. PCT/IL2018/050925, dated Dec. 17, 2018, 13 pgs.

*Primary Examiner* — Jay B Shah
(74) *Attorney, Agent, or Firm* — Cantor Colburn LLP

(57) ABSTRACT

A device for measuring a concentration of a component in a target sample includes a flow chamber with a first channel that receives a reference sample having a known concentration of the component. The flow chamber also includes a second channel that receives the target sample having an unknown concentration of the component. A pump operates to pump the reference sample and the target sample at a same volume flow rate through the first and second channels, respectively. A thermal mass flow meter measures a thermal conductivity of the reference sample, a thermal conductivity of the target sample, or both.

20 Claims, 2 Drawing Sheets

(51) Int. Cl.

| | |
|---|---|
| *A61M 16/08* | (2006.01) |
| *G01N 25/18* | (2006.01) |
| *G01N 33/497* | (2006.01) |
| *G01N 33/00* | (2006.01) |
| *B81B 7/02* | (2006.01) |
| *H01L 41/08* | (2006.01) |
| *A61B 5/087* | (2006.01) |
| *A61B 5/00* | (2006.01) |
| *A61B 5/08* | (2006.01) |
| *A61M 16/04* | (2006.01) |

(56) References Cited

U.S. PATENT DOCUMENTS

| | | |
|---|---|---|
| 2011/0247390 A1 | 10/2011 | Smirnov et al. |
| 2014/0275857 A1 | 9/2014 | Toth et al. |

FOREIGN PATENT DOCUMENTS

| | | |
|---|---|---|
| JP | H0545285 A | 2/1993 |
| WO | 2011138774 A1 | 11/2011 |
| WO | 2017019783 A1 | 2/2017 |

DEVICE, SYSTEM AND METHOD FOR THERMAL CAPNOGRAPHY

CROSS-REFERENCE TO RELATED APPLICATION

This application claims priority to and the benefit of U.S. Provisional Application No. 62/551,302, entitled "DEVICE, SYSTEM AND METHOD FOR THERMAL CAPNOGRAPHY," filed Aug. 29, 2017, the content of which is incorporated herein by reference in its entirety for all purposes.

TECHNICAL FIELD

The disclosure generally relates to devices, systems and methods for thermal conductivity based determination of the concentration of a fluid component in a fluid sample.

BACKGROUND

This section is intended to introduce the reader to various aspects of art that may be related to various aspects of the present techniques, which are described and/or claimed below. This discussion is believed to be helpful in providing the reader with background information to facilitate a better understanding of the various aspects of the present disclosure. Accordingly, it should be understood that these statements are to be in this light, and not as admissions of prior art.

Thermal mass flow meters, also known as thermal dispersion or immiscible mass flow meters, include a family of instruments for measurement of a total mass flow rate of a fluid, primarily gases, flowing through closed conduits. Thermal mass flow meters measure the total mass flow rate of the fluid based on heat transferred via convection from a heated surface to the fluid. The heat is transferred to a boundary layer of the fluid as the fluid flows over the heated surface.

SUMMARY

The present disclosure relates to devices, systems and methods for measuring a concentration of a component in a target sample based on a thermal signature of the component measured using a thermal mass flow meter, for example.

The thermal mass flow meter is configured to measure a total mass flow rate of a fluid (e.g., a gas) based on heat transferred via convection from a heated surface to the fluid. The heat is transferred to a boundary layer of the fluid as the fluid flows over the heated surface. The thermal mass flow meter may include two spaced apart temperature sensors and a heating element positioned between the temperature sensors, such that a fluid flowing from the first temperature sensor to the second temperature sensor will receive heat from the heating element during flow. As different fluids have different thermal conductivities, the convective heat transfer differs between different fluids. For example, the thermal conductivity of ambient air at 25 degrees Celsius is 0.024 Watts per meter-Kelvin (W/[m*K]), whereas the thermal conductivity of $CO_2$ at 25 degrees Celsius is 0.0146 W/(m*K). Thus, thermal mass flow meters enable the calculation of a concentration of a component in a target fluid (e.g., the concentration of $CO_2$ in exhaled breath) by measuring a temperature differential between the target fluid (e.g., exhaled breath) and a reference fluid (e.g., a fluid having a known concentration of the components, such as ambient air, which has a known concentration of $CO_2$).

Advantageously, the herein disclosed devices, systems and methods utilize respective thermal signatures (e.g., thermal conductivity at a given temperature) of a reference fluid (e.g., ambient air) and a component (e.g., $CO_2$) to detect a concentration of the component within a target fluid (e.g., exhaled breath). The device includes a pump that provides a defined flow (e.g., volumetric flow rate) of the target fluid through a channel of a flow chamber, and a thermal mass flow meter that measures the thermal conductivity of the target fluid. The pump may also provide a defined flow (e.g., volumetric flow rate) of a reference fluid (e.g., ambient air) having a known composition (e.g., known concentration of the component) and a known thermal conductivity through another channel of the flow chamber, and the thermal mass flow meter may measure the thermal conductivity of the reference fluid. Based on the measured temperature differentials of the reference fluid and the target fluid, as well as the defined flow rate and temperature of the fluids, the composition of the target fluid (e.g., the concentration of the component, such as the $CO_2$ concentration) may be determined. More specifically, because the thermal conductivity of the sampled gas is approximately linearly correlated with the concentration of the component in the target sample, the device may determine a difference in mass flow rate between the target sample and the reference sample based on the outputs of the thermal mass flow meter(s) (e.g., the mass flow rate of the target sample and the mass flow rate of the reference sample), and then the device may correlate the difference in mass flow rate to the concentration of the component in the target sample.

Advantageously the device may be formed as a microfluid system in which the thermal mass flow meter measures the temperature differential across a microelectromechanical (MEMS) chip, such as, but not limited to, a silicon-based MEMS chip. The device can thus be of extremely small scale (e.g., in the range of 0.02 millimeter [mm] to 1 mm).

In addition, the device may be devoid of expensive components, and thus may have low production costs. An additional advantage is the efficient power consumption of the device, which may be in an order of 10 milliwatts (mW), ensuring low cost of use.

According to some embodiments, the thermal mass flow meter may be a high-frequency thermal mass flow meter that is sufficient to enable essentially continuous, monitoring of the $CO_2$ concentration in the subject's exhaled breath, thereby providing an efficient evaluation of the subject's respiratory status.

According to some embodiments, a device configured to measure a concentration of a component in a target sample includes a flow chamber with a first channel configured to receive a reference sample (e.g., having a known concentration of the component), and a second channel configured to receive the target sample having an unknown concentration of the component. The device also includes at least one pump configured to pump the reference sample and the target sample, at a same volumetric flow rate, through the first and second channels, respectively. The device further includes a first thermal mass flow meter configured to measure a thermal conductivity of the reference sample or the target sample.

According to some embodiments, the device may further include a second thermal mass flow meter. In such cases, the first thermal mass flow meter may be configured to measure the thermal conductivity of the reference sample, and the second thermal mass flow meter may be configured to measure the thermal conductivity of the target sample.

According to some embodiments, the device may further include a processing unit configured to calculate the concentration of the component in the target sample based on an integrated analysis of the thermal conductivity measured for the reference sample and the thermal conductivity measured for the target sample. According to some embodiments, the processing unit may be an integral part of the device. According to some embodiments, the processing unit may be a stand-alone unit. According to some embodiments, the processing unit may further be configured to calculate the concentration of the component in the target sample based on the temperature of the reference sample and/or the temperature of the target sample measured by the temperature sensor.

According to some embodiments, the pump may be a dual-chamber piezoelectric pump.

According to some embodiments, the target sample may be exhaled breath and the component may be CO2. According to some embodiments, the reference sample may be ambient air.

According to some embodiments, the device may be incorporated into a MEMS device.

According to some embodiments, the device may further include a communication link configured to transmit the thermal conductivity of the reference sample and/or thermal conductivity of the target sample, as measured by one or more thermal mass flow meters, to the processing unit.

According to some embodiments, the device may further include a heating and/or cooling element configured to adjust a temperature (e.g., heat and/or cool) of the reference sample and/or the target sample to a same temperature prior to entry of the reference sample and/or the target sample into the flow chamber.

According to some embodiments, the device may further include a temperature sensor configured to measure the temperature of the reference sample and/or the target sample prior to entry of the reference sample and/or the target sample into the flow chamber.

According to some embodiments, a method for measuring a concentration of a component of a target sample includes generating a flow of a reference sample, having a known concentration of the component, at a predetermined volumetric flow rate. The method also includes measuring a thermal conductivity of the reference sample using a thermal mass flow meter. The method further includes generating a flow of a target sample having an unknown concentration of the component at the same predetermined volumetric flow rate, and measuring the thermal conductivity of the target sample using a thermal mass flow meter. The method further includes calculating the concentration of the component in the target sample based on an integrated analysis of the thermal conductivity of the reference sample and the thermal conductivity of the target sample, as measured via the thermal mass flow meters.

According to some embodiments, measuring the thermal conductivity of the reference sample may be conducted prior to measuring of the thermal conductivity of the target sample. According to some embodiments, measuring the thermal conductivity of the reference sample may be conducted at a first set of predetermined time intervals, and measuring the thermal conductivity of the target sample may be conducted at a second set of predetermined time intervals. According to some embodiments, the first and second set of predetermined time intervals may be the same or different.

According to some embodiments, the target sample may be exhaled breath and the component may be CO2.

According to some embodiments, a computer-readable medium stores instructions that, when executed, cause a processing unit to establish a connection with a microprocessor of a MEMS device and to transmit a signal to the microprocessor. The signal may activate a pump, a first thermal mass flow meter, and a second thermal mass flow meter (some or all of which may be incorporated onto or fabricated on the MEMS chip). Thereafter, the pump may generate a flow of a reference sample, having a known concentration of a component, towards the first thermal flow meter. The pump may also generate a flow of a target sample, having an unknown concentration of the component, towards the second thermal flow meter. The first and second thermal mass flow meters may conduct thermal conductivity measurements on the reference sample and the target sample, respectively. The microprocessor may receive the measured thermal conductivity of the reference sample and the measured thermal conductivity of the target sample, through the connection established between the MEMS device and the microprocessor. The microprocessor may calculate a concentration of the component in the target sample, based on an integrated analysis of the measured thermal conductivity of the reference sample and the measured thermal conductivity of the target sample.

According to some embodiments, the flow of the reference sample and the flow of the target sample may be physically separated. According to some embodiments, the volumetric flow rate of the reference sample may be generally identical (e.g., within 0.5, 1, 2, 3, 4, or 5 percent) of the volumetric flow rate of the target sample.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

In addition to the exemplary aspects and embodiments described above, further aspects and embodiments will become apparent by reference to the figures and by study of the following detailed descriptions.

BRIEF DESCRIPTION OF THE FIGURES

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

DETAILED DESCRIPTION

Figure 1:
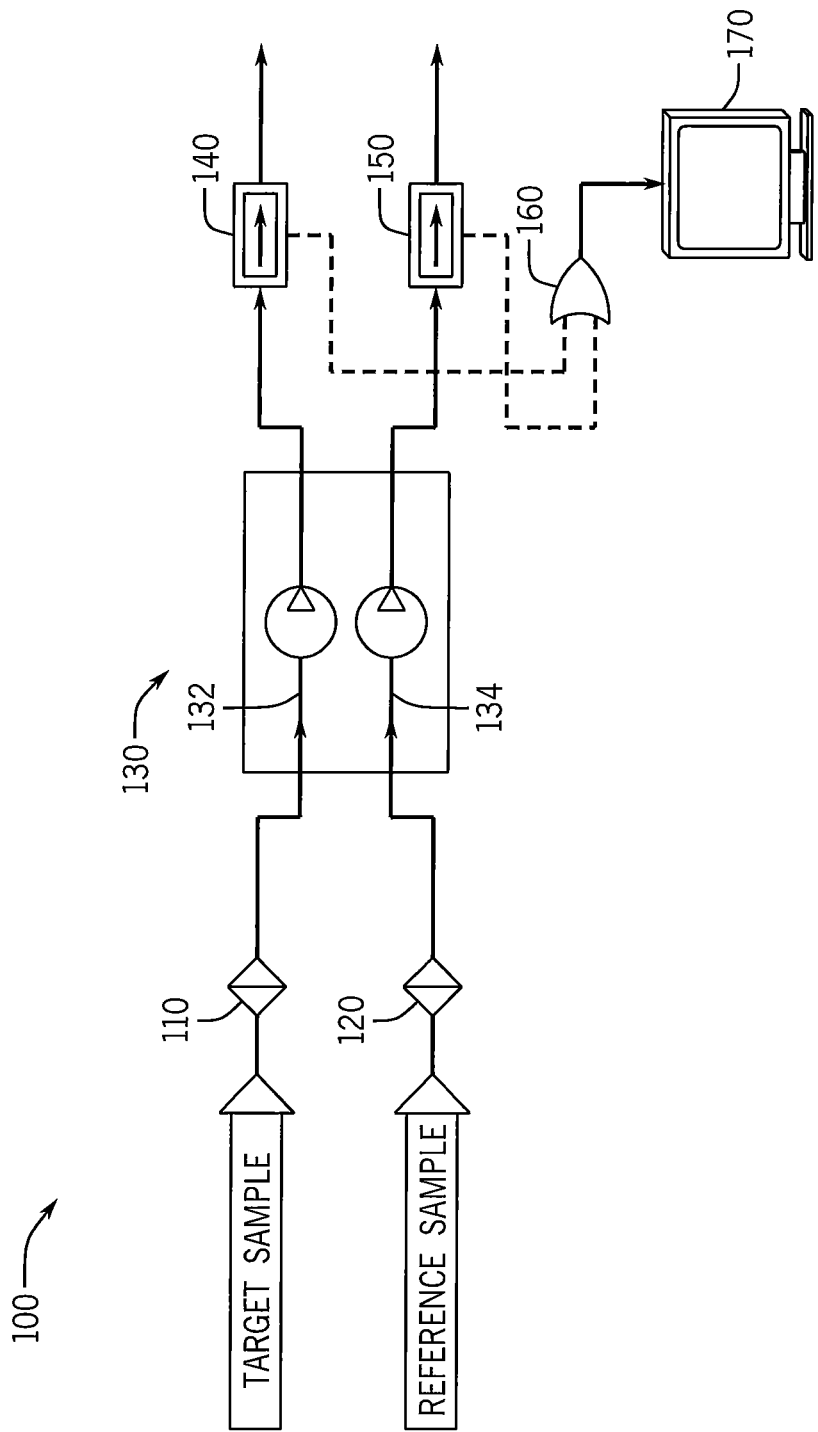
FIG. 1 schematically illustrates a thermal mass flow measurement (MFM) system for measuring a concentration of a component in a target sample, according to an embodiment of the present disclosure.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

According to some embodiments, a device for measuring a concentration of a component in a target sample includes a flow chamber having a first channel configured to receive a reference sample having a known concentration of the component and a second channel configured to receive the target sample having an unknown concentration of the component. At least one pump is configured to produce a same volumetric flow for the reference sample and the target sample through the first and second channels, respectively. One or more thermal mass flow meters are configured to measure a thermal conductivity of the reference sample and/or a thermal conductivity of the target sample.

As used herein, the term "fluid" may refer to a subset of the phases of matter including liquids, gases, and plasmas, characterized by not being resistant to shear forces. According to some embodiments, the fluid may be a reference fluid, such as, but not limited to, ambient air and/or another sample having a known concentration of the component of interest. According to some embodiments, the fluid may be a target fluid (e.g., a fluid for which the composition is subject to analysis, such as, but not limited to, exhaled breath). According to some embodiments, the component may be a specific component, which is present in the target sample, such as, but not limited to, the $CO_2$ concentration in a subject's exhaled breath. According to some embodiments, more than one component may be subject to analysis (e.g., 2, 3, 4 or more components). It should be understood that in cases where more than one component is being analyzed it may be advantageous to utilize more than one reference sample, each reference sample having a different, but known, concentration of the individual component, in order to facilitate a reliable calculation of the concentration of the individual component. Each possibility and combination of possibilities is a separate embodiment.

As used herein, the term "flow chamber" may refer to a compartment configured to receive the fluid samples (e.g., the target sample and the reference sample) and to enable performance of an analysis (e.g., thermal conductivity measurements). According to some embodiments, the chamber may include at least two flow channels. As used herein, the term "channels," "chambers," and "tubes" may be used interchangeably and may refer to conduits enabling the flow chamber to receive two or more different samples (e.g., a reference sample and a target sample) and to allow their separate analysis (e.g., determination of their respective thermal conductivity). According to some embodiments, the channels may be separate, defined channels (e.g., tubes) running through the flow chamber. Alternatively, the channels may be formed, for example, by splitting of the flow chamber into sub-chambers, for example, by a membrane. According to some embodiments, the channels may have an internal diameter of less than 1 mm or less than 0.5 mm, for example. According to some embodiments, the device may include more than one flow chamber and/or each flow chamber may include more than two flow channels (e.g., 3, 4, 5, 6 or more flow channels), which may facilitate measurement of more than one component. Each possibility is a separate embodiment.

As used herein, the term "pump" may refer to any pump configured to ensure a same (e.g., within 0.5, 1, 2, 3, 4, or 5 percent) defined volumetric flow rate of the target fluid and the reference fluid through the flow chamber. It is understood that utilizing a standard pump, which does not ensure a same defined volumetric flow rate of the target fluid and the reference fluid, may also be a possibility, in which case the device should further include a non-thermal flow sensor configured to determine the flow rate of each of the reference sample and the target sample in a temperature independent manner. The thermal conductivity measured by the thermal mass flow meter may then be normalized based on the flow rate measured by the non-thermal flow sensor.

According to some embodiments, the pump may be external to the flow chamber. According to some embodiments, the pump may be an integral part of the flow chamber. According to some embodiments, the pump may be a diaphragm pump. According to some embodiments, the diaphragm may be a piezoelectrically actuated diaphragm. According to some embodiments, the pump may be a dual-chamber piezoelectric pump. According to some embodiments, the dual-chamber piezo-electric pump a may be a micropump (e.g., having a volume below 200 $mm^3$, below 150 $mm^3$ or below 100 $mm^3$). According to some embodiments, the piezoelectric pump may be a miniature, low power, and chemically resistant stainless-steel diaphragm pump with a piezoelectric actuation mechanism. According to some embodiments, the piezoelectric pump may include a piezoelectric diaphragm and a valve. According to some embodiments, the piezoelectric pump may include two valves, such as, but not limited to, two passive check valves, positioned on both sides of the pump chamber, thereby defining the direction of the flow. According to some embodiments, the piezoelectric diaphragm may include a piezo ceramic mounted on a coated brass membrane, such that when voltage is applied, the membrane is deformed (e.g., a downstroke in the membrane), thus causing gases in the pump chamber to be ejected therefrom. Similarly, when the voltage decreases, an opposite deformation (e.g., upstroke) of the membrane occurs, causing gas to be sucked into the pump chamber, thus refilling the pump chamber. According to some embodiments, the pump can perform several hundred (e.g., 200, 300 or 500) pumping cycles per second. According to some embodiments, the pumping performance and/or the flow rate may be adjusted by changing electrical, mechanical and/or pneumatic parameters of the pump. Non-limiting examples of optional electrical, mechanical and/or pneumatic parameters include number and/or geometry of the piezo-crystal electrodes, pump chamber volume, applied voltage and/or frequency or any other suitable parameter or combination of parameters.

According to some embodiments, the pump includes a control board (e.g., a printed circuit board [PCB]) configured to enable control of the pump from a remote processing device, such as, but not limited to, a PC, for example through a USB port.

As used herein, the terms "thermal mass-flow meter," "thermal flow meter," "dispersion mass flow meter" and "immiscible mass flow meter" may be used interchangeably and may refer to a sensor configured to measure a volumetric flow rate of a fluid (e.g., a gas) by means of the heat convected from a heated surface to the fluid as the fluid flows over the heated surface. The heat is transferred to a boundary layer of the fluid as the fluid flows over the heated surface. According to some embodiments, the thermal mass flow meter may include two spaced apart temperature sensors and a heating element positioned between the temperature sensors. A fluid flowing from the first temperature sensor to the second temperature sensor will receive the heat from the heating element, and thus, a first temperature of the fluid measured by the first temperature sensor will be different (e.g., lower) than a second temperature of the fluid measured by the second temperature sensor.

According to some embodiments, the device may further include at least two thermal mass flow meters, each of the thermal mass flow meters functionally connected to the first and second channels, respectively. For example, a first thermal mass flow meter may be configured to measure the thermal conductivity of a reference sample flowing in one channel, and the second thermal mass flow meter may be configured to measure the thermal conductivity of the target sample flowing in another channel. According to some embodiments, the measurement of the thermal conductivity of the reference sample and the target sample may be simultaneous. Additionally or alternatively, the measurement of the thermal conductivity of the reference sample and the target sample may be consecutive. According to some embodiments, the measurement of the thermal conductivity of the reference sample may be performed prior to the measurement of the thermal conductivity of the target sample. According to some embodiments, the measurement of the thermal conductivity of the reference sample may be performed once (e.g., upon powering on the device, upon input by an operator [e.g., medical professional], during an initial monitoring period for the subject), to determine a reference thermal conductivity to which subsequent measurements on the target sample will be compared. According to some embodiments, the measurement of the thermal conductivity of the reference sample may be performed at predetermined time intervals during a monitoring session (e.g., every 1, 2, 3, 4, 5, 10, 60, 120 or more minutes) and/or upon input by an operator and/or upon other input (e.g., indicative of a change in location of the subject). According to some embodiments, the measurement of the thermal conductivity of the target sample and/or the reference sample may be performed continuously.

According to some embodiments, the device may further include a processing unit, configured to calculate the concentration of the component in the target sample, based on an integrated analysis of the thermal conductivity measured for the reference sample and the thermal conductivity measured for the target sample, given the defined temperature and volumetric flow rates of the samples. In some embodiments, the measured thermal conductivity of the target sample may be linearly correlated with its composition. Accordingly, the composition of the target sample may be extrapolated from the difference between the thermal conductivity of the reference sample and the thermal conductivity of the target sample. It should be appreciated that filters (e.g., band-pass filters) may be applied to filter noise as part of the processing steps.

According to some embodiments, the processing unit may be a dedicated monitor, a PC, a laptop, a smart phone, or a virtual (e.g., cloud based) processing unit. Each possibility is a separate embodiment.

According to some embodiments, the processing unit may be an integral part of the device. Additionally or alternatively, the processing unit, or parts thereof, may be stand-alone components. According to some embodiments, the device may include a communication link configured to transmit the measured thermal conductivities of the reference sample and/or the target sample to the processing unit. According to some embodiments, the processing unit may include a display configured to display the concentration of the component and/or the measured thermal conductivities, for example.

According to some embodiments, the device may be incorporated onto or be fabricated on MEMS component. According to some embodiments, the MEMS is made up of components between 1 and 100 micrometers in size (i.e., 0.001 to 0.1 mm), and has a size in the range of 20 micrometers to 1 mm (i.e., 0.02 to 1.0 mm). According to some embodiments, the MEMS includes a central unit that processes data (e.g., microprocessor) and several components that interact with the surroundings, such as microsensors, such as the thermal mass flow meter, and the pump.

According to some embodiments, the device may further include a heating element and/or a cooling element configured to adjust a temperature (e.g., heat and/or cool) the reference sample and/or the target sample to a same (e.g., within 0.5, 1, 2, 3, 4, or 5 percent), optionally predetermined, temperature prior to entering the flow chamber. The thermal conductivity of a fluid may depend on the temperature of the fluid. Equalizing the temperatures of the target sample and the reference sample prior to their analysis by the thermal flow meter may thus facilitate efficient and reliable comparison of the samples and the extrapolation of the concentration of a component of interest in the target sample. Additionally, or alternatively, the device may include a temperature sensor configured to measure the temperature of the reference sample and/or the target sample prior to entering the flow chamber. This enables calculating the concentration of the component in the target sample while taking into consideration differences in the temperature of the samples as they enter the flow chamber. Additionally, or alternatively, the first temperature sensor(s) in the thermal mass flow meter(s) may be utilized to measure the temperature of the reference sample and/or the target sample prior passing over the heat source(s) within the thermal mass flow meter(s). This enables calculating the concentration of the component in the target sample while taking into consideration differences in the initial temperature of the samples prior to measuring the thermal conductivities.

According to some embodiments, there is provided a method for measuring a concentration of a component in a target sample, and the method includes generating a flow of a reference sample, having a known composition, at a predetermined volumetric flow rate through a flow chamber, and measuring the thermal conductivity of the reference sample using a thermal mass flow meter. The method further includes generating a flow of a target sample, having an unknown concentration of a component (e.g., $CO_2$) for which the thermal conductivity is known, at the same predetermined volumetric flow rate as the reference sample, through a second compartment of the flow chamber, and measuring the thermal conductivity of the target sample using the same or a different thermal mass flow meter. The concentration of the component in the target sample may then be determined based on an integrated analysis of the measured thermal conductivities of the reference sample and the target sample, given the known volumetric flow rate and temperature of the samples.

According to some embodiments, the method may be conducted utilizing the herein disclosed device for measuring a concentration of a component of a target fluid.

According to some embodiments, the timing for measuring the thermal conductivity of the reference sample may be as essentially described herein. For example, according to some embodiments, the measurements on the reference sample may be conducted prior to the commencement of the monitoring of the target sample. Thereafter, the thermal conductivity of the reference sample can serve as a baseline for the subsequent measurements performed on the target sample, and thus, for the determination of the concentration of one or more components in the target sample. As another non-limiting example, the measurements on the reference sample may be conducted at predetermined time intervals (e.g. every 1, 2, 3, 4, 5, 10, 60, 120 or more minutes), while the measurements on the target sample may be performed at a higher frequency (e.g., every 0.25, 0.5, 1, 2, 3, or more minutes) or even continuously. As another non-limiting example, the measurements on the reference sample and the target sample may be performed essentially simultaneously and optionally continuously.

According to some embodiments, there is provided computer-readable medium storing instructions that, when executed, cause a processing unit to establish a connection with a microprocessor, such as, but not limited to, a microprocessor of a MEMS chip. The instructions cause a processing unit to transmit a signal to the microprocessor, and the signal activates a pump, a first thermal flow meter, and a second thermal flow meter (some or all of which may be incorporated onto or fabricated on the MEMS chip). As a result, a flow of a reference sample toward the first thermal flow meter, and a flow of a target sample toward the second thermal flow meter may be initiated and thermal conductivity measurements by the first and second thermal flow meters may be conducted.

According to some embodiments, the computer-readable medium may further store instructions that, when executed cause the processing unit to receive the measured respective thermal conductivities of the reference sample and the target sample through the connection established with the microprocessor, and to calculate a concentration of a component in the target sample based on an integrated analysis of the thermal conductivity of the reference sample and the thermal conductivity of the target sample and the known volumetric flow rate and temperature of the samples.

According to some embodiments, the flow of the reference sample and the flow of the target sample may be physically separated, for example, as essentially described herein. According to some embodiments, the volumetric flow rate of the reference sample may be essentially identical to the volumetric flow rate of the target sample, as essentially described herein. Alternatively, the MEMS device may further include a non-thermal flow sensor configured to determine the flow of the reference sample and the flow of the target sample in a temperature independent manner, in which case the computer-readable medium may further store instructions that, when executed, cause the processing unit to normalize the thermal conductivity measured, based on the flow rate measured by the non-thermal flow sensor.

According to some embodiments, the pump may be a piezoelectric pump. According to some embodiments, the piezoelectric pump may be a dual chamber piezoelectric pump, as essentially described herein.

According to some embodiments the MEMS may have a size in the range of 0.02 mm to 1.0 mm, as essentially described herein.

Reference is now made to FIG. 1, which schematically illustrates a thermal mass flow measurement (MFM) system 100 for measuring a concentration of a component (e.g., $CO_2$) in a target sample (e.g., exhaled breath). The MFM system 100 includes a first inlet 110 configured to receive the target sample (e.g., a sample including a component, the concentration of which is the target of the monitoring, such as exhaled breath), and a second inlet 120 configured to receive a reference sample (e.g., a sample having a known concentration of the component of interest, such as ambient air). The MFM system 100 further includes a pump, such as a dual-chamber piezoelectric pump 130 having a first chamber 132 (e.g., a tube or channel having an inner diameter of below 0.5 mm) configured to receive the target sample and a second chamber 134 (e.g., a second tube or channel having an inner diameter of below 0.5 mm) configured to receive the reference sample. Advantageously, the piezoelectric pump 130 is configured to produce the same volumetric flow in both the first chamber 132 and the second chamber 134. The first chamber 132 includes or is fluidly connected to a first thermal mass flow meter (thermal MFM) 140 configured to measure the thermal conductivity of the target sample. The second chamber 134 includes or is fluidly connected to a second thermal mass flow meter (thermal MFM) 150 configured to measure the thermal conductivity of the reference sample. Since the thermal conductivity of ambient air (e.g., 0.024 W/[m*K] at 25 degrees Celsius) and the thermal conductivity of the component of interest (e.g., $CO_2$, 0.0146 W/(m*K) at 25 degrees Celsius) are known, a processor and/or computing unit 160 can calculate/extrapolate the concentration of the component in the target sample based on the differential thermal conductivity of the target sample as compared to that of reference sample. As the thermal conductivity measurements are temperature dependent, the MFM system 100 may optionally further include a heating/cooling element configured to adjust a temperature (e.g., heat and/or cool) the target sample and/or the reference sample to a predetermined temperature (e.g. 25° C.) prior to the samples reaching dual-chamber piezoelectric pump 130, and/or the first thermal MFM 140 and the second thermal MFM 150, respectively. The MFM system 100 may optionally further include a display 170 configured to display the determined concentration of the component in the target sample (e.g., the concentration of $CO_2$ in exhaled breath) and optionally the measured thermal conductivity of the target sample and/or the measured thermal conductivity of the reference sample. According to some embodiments, the MFM system 100 may be configured to continuously determine the concentration of the component in the target sample over a plurality of breath cycles, thereby enabling calculation of the concentration of $CO_2$ in exhaled breath over time. According to some embodiments, a curve depicting the concentration of the component over time (e.g., similar to a capnogram depicting the partial pressure of $CO_2$ over time) may be displayed on display 170. According to some embodiments, at least parts of the MFM system 100 (e.g., the first inlet 110, the second inlet 120, the piezoelectric pump 130, the first thermal MFM 140, the second thermal MFM 150 and optionally the processing unit 160 or parts thereof) may be part of a MEMS device. This advantageously provides a small, wearable, low cost, and power saving monitor (e.g., $CO_2$ monitor).

Figure 2:
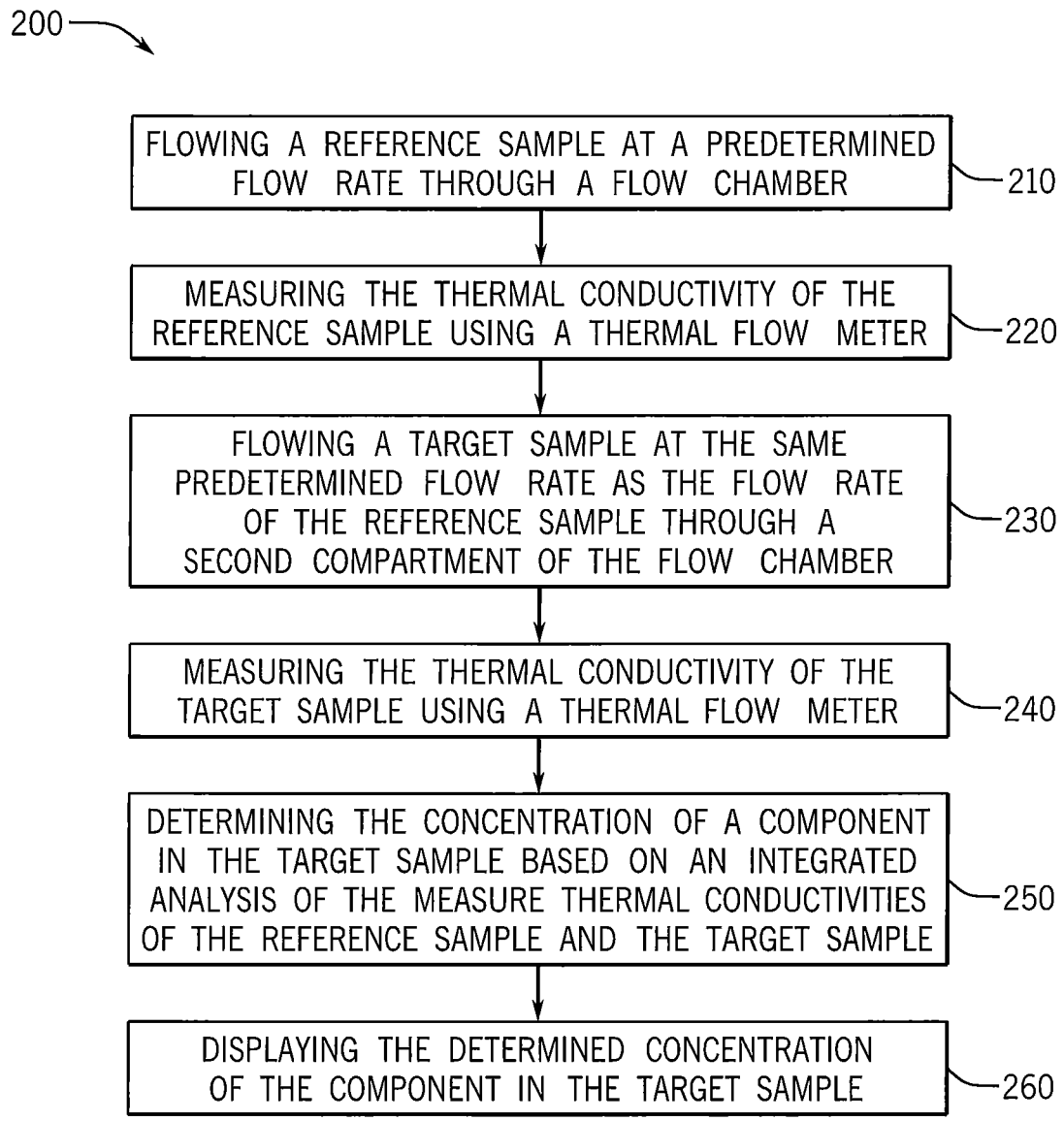
FIG. 2 is a flow chart of a method for measuring a concentration of a component in a target sample using the MFM system of FIG. 1, in accordance with an embodiment of the present disclosure.

Reference is now made to FIG. 2, which is an illustrative flow chart of a method 200 for measuring a concentration of a component in a target sample, according to some embodiments. In step 210, a reference sample (e.g., ambient air) having a known concentration of a component (e.g., $CO_2$) flows at a predetermined volumetric flow rate through a flow chamber, such as a flow chamber of a dual-chamber piezoelectric pump. In step 220, the thermal conductivity of the reference sample is measured using a thermal flow meter. In step 230, which may be performed simultaneously with or subsequently to steps 210 and 220, a target sample (e.g., exhaled breath) having an unknown concentration of the component (e.g., $CO_2$) may flow at the same predetermined volumetric flow rate, as the volumetric flow rate of the reference sample, through a second compartment of the flow chamber, such as a second flow chamber of a dual-chamber piezoelectric pump. In step 240, the thermal conductivity of the target sample may be measured by a second thermal mass flow meter. In step 250, the concentration of the component (e.g., $CO_2$) in the target sample (e.g., exhaled breath) may then be determined based on an integrated analysis of the measured thermal conductivities of the reference sample and the target sample, the known volumetric flow rate of the samples and their temperature. According to some embodiments, the method 200 may optionally further include a step 260 of displaying the determined concentration of the component in the target sample, the change in the concentration of the component over time, and/or a trend in the change in the concentration of the component over time.

It is understood that the some of the steps set forth may be consecutive while others may be executed simultaneously. As briefly explained, the timing of steps the measurement performed on the reference sample may be conducted prior to the commencement of the monitoring of the target sample, and thereafter, the reference measurements serve as a baseline for the subsequent measurements performed on the target sample and for the determination of the concentration of the component in the target sample. As another non-limiting example, the measurements on the reference sample may be conducted at predetermined time intervals while the measurements on the target sample may be performed smaller predetermined time intervals or continuously. As another non-limiting example, the measurements on the reference sample and the target sample may be performed essentially simultaneously and/or continuously.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" or "comprising", when used in this specification, specify the presence of stated features, integers, steps, operations, elements, or components, but do not preclude or rule out the presence or addition of one or more other features, integers, steps, operations, elements, components, or groups thereof. According to some embodiments, the term "comprising" may be replaced by the term "consisting essentially of" or "consisting of".

The device may be described in the general context of computer-executable instructions, such as program modules, being executed by a computer. Generally, program modules include routines, programs, objects, components, data structures, and so forth, which perform particular tasks or implement particular abstract data types. The techniques disclosed herein may also be practiced in distributed computing environments where tasks are performed by remote processing devices that are linked through a communications network. In a distributed computing environment, program modules may be located in both local and remote computer storage media including memory storage devices.

Unless specifically stated otherwise, as apparent from the following discussions, it is appreciated that throughout the specification discussions utilizing terms such as "processing," "computing," "calculating," "determining," "estimating," or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The processes and displays presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below. In addition, embodiments of the present disclosure are not described with reference to any particular programming language. It will be appreciated that a variety of programming languages may be used to implement the teachings of the embodiments as described herein.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. A device for measuring a concentration of a component in a target sample, the device comprising:
   a flow chamber comprising a first channel configured to receive a reference sample having a known concentration of the component and a second channel configured to receive the target sample having an unknown concentration of the component;
   at least one pump configured to pump the reference sample and the target sample, at a same volume flow rate, through the first and second channels, respectively; and
   at least a first thermal mass flowmeter configured to measure a thermal conductivity of the reference sample, a thermal conductivity of the target sample, or both.

2. The device of claim 1, comprising a second thermal mass flow meter, wherein the first thermal mass flow meter is configured to measure the thermal conductivity of the reference sample, and the second thermal mass flow meter is configured to measure the thermal conductivity of the target sample.

3. The device of claim 1, wherein the pump is a dual-chamber piezoelectric pump.

4. The device of claim 1, wherein the target sample is exhaled breath and wherein the component is $CO_2$.

5. The device of claim 1, wherein the reference sample is ambient air.

6. The device of claim 1, wherein the device is incorporated into a microelectromechanical systems (MEMS) device.

7. The device of claim 1, comprising a processing unit configured to calculate the concentration of the component in the target sample based on an integrated analysis of the thermal conductivity of the reference sample and the thermal conductivity of the target sample.

8. The device of claim 7, wherein the processing unit is an integral part of the device.

9. The device of claim 7, wherein the processing unit is a stand-alone unit.

10. The device of claim 9, comprising a communication link configured to transmit the thermal conductivity the reference sample, the thermal conductivity of the target sample, or both, to the processing unit.

11. The device of claim 1, comprising a heating/cooling element configured to adjust a temperature of the reference sample and the target sample to a same temperature prior to entering the flow chamber.

12. The device of claim 1, comprising one or more temperature sensors configured to measure a temperature of the reference sample, a temperature of the target sample, or both, prior to entry of the reference sample, the target sample, or both, into the flow chamber.

13. The device of claim 12, comprising a processing unit configured to calculate the concentration of the component in the target sample based on an integrated analysis of the thermal conductivity of the reference sample and the thermal conductivity of the target sample, wherein the processor is configured to calculate the concentration of the component in the target sample based on the temperature of the reference sample, the temperature of the target sample, or both, as measured by the one or more temperature sensors.

14. A method for measuring a concentration of a component of a target sample, the method comprising:
generating a flow of a reference sample, having a known concentration of the component, at a predetermined volumetric flow rate;
measuring a thermal conductivity of the reference sample using a first thermal mass flow meter;
generating a flow of a target sample having an unknown concentration of the component at the same predetermined volumetric flow rate;
measuring a thermal conductivity of the target sample using the first thermal mass flow meter or a second thermal flow meter; and
calculating the concentration of the component in the target sample based on an integrated analysis of the thermal conductivity of the reference sample and the thermal conductivity of the target sample.

15. The method of claim 14, wherein measuring the thermal conductivity of the reference sample is conducted prior to measuring the thermal conductivity of the target sample.

16. The method of claim 14, wherein measuring the thermal conductivity of the reference sample is conducted at a first set of predetermined time intervals, and measuring the thermal conductivity of the target sample is conducted at a second set of predetermined time intervals.

17. The method of claim 16, wherein the first and second set of predetermined time intervals are different.

18. The method of claim 14, wherein the target sample is exhaled breath and the component is $CO_2$.

19. A non-transitory computer-readable medium storing instructions that, when executed, cause a processing unit to: establish a connection with a microprocessor of a microelectromechanical systems (MEMS) device; transmit a signal to the microprocessor, the signal activating a pump, a first thermal mass flow meter, and a second thermal mass flow meter incorporated onto the MEMS device, thereby: generating a flow of a reference sample, having a known concentration of a component, toward the first thermal flow meter and a flow of a target 21 sample, having an unknown concentration of the component, toward the second thermal flow meter, wherein the flow of the reference sample and the flow of the target sample are physically separated, and the volumetric flow rate of the reference sample is essentially identical to the volumetric flow rate of the target sample; and measuring a thermal conductivity of the reference sample and a thermal conductivity of the target sample utilizing the first and second thermal mass flow meters, respectively; wherein the instructions, when executed, cause the processing unit to receive the thermal conductivity of the reference sample and the thermal conductivity of the target sample through the connection established with the microprocessor, and to calculate a concentration of the component in the target sample based on an integrated analysis of the thermal conductivity of the reference sample and the thermal conductivity of the target sample.

20. The non-transitory computer-readable medium of claim 19, wherein the instructions, when executed, cause the processing unit to instruct a display to display the concentration of the component.

* * * * *